United States Patent [19]

Fredriksson

[11] 3,966,924

[45] June 29, 1976

[54] COMPOSITION AND METHOD FOR TREATING PSORIASIS

[75] Inventor: Torsten Fredriksson, Vasteras, Sweden

[73] Assignee: Allergan Pharmaceuticals, Irvine, Calif.

[22] Filed: Nov. 13, 1974

[21] Appl. No.: 523,241

[52] U.S. Cl. .............................................. 424/240
[51] Int. Cl.² ......................................... A61K 31/56
[58] Field of Search ................. 260/397.45; 424/240

[56] References Cited
OTHER PUBLICATIONS

Fisher et al., "Psoriasis", Proc. Int. Symp. (1971) pp. 335–345, CA. vol. 79, pp. 49, 360m abstracted.

Stroughton et al., "Psoriasis", Proc. Int. Symp. (1971) pp. 367–375, CA. vol. 79, Par. 38,717h.

Tissot et al., "Acta Dermato–Venereol", vol. 46(5), (1966) pp. 447–452, Abstracted CA. vol. 66 (1967) p. 9621v.

*Primary Examiner*—Elbert L. Roberts
*Attorney, Agent, or Firm*—Martin A. Voet

[57] ABSTRACT

A composition and method for treating psoriasis in humans comprising the topical administration to a human suffering from psoriasis of an effective dose for treating psoriasis of a composition comprising from about 0.01 to about 5% of a corticosteroid and preferably a halogenated corticosteroid and from about 0.05 to about 10% of 5-fluorouracil together with a suitable topical carrier.

4 Claims, No Drawings

COMPOSITION AND METHOD FOR TREATING PSORIASIS

BACKGROUND OF THE INVENTION

Field of the Invention

The present invention relates to the therapeutic treatment of proliferation-type skin diseases. More particularly, the present invention relates to the use of corticosteroids in combination with 5-fluorouracil in the treatment of skin conditions such as psoriasis.

Psoriasis is a common, chronic, relapsing disease of unknown etiology which consists of elevated, silvery, dry lesions which are known as plaques. Pathologically, there are three obvious changes associated with the disease: (1) increase in the rate of cell division of the epidermis, (2) striking increase in the thickness of the cornified epithelium, and (3) proliferation of the subepithelial capillaries.

Corticosteroids and especially halogenated corticosteroids have been successfully used in the topical treatment of psoriasis to temporarily alleviate the signs and symptoms of the disease. This effect is probably due to influence on the nucleic acid metabolism of the epidermis. The effect, which is most striking when occlusive dressings are used, is now well documented and accepted. However, there are several disadvantages with this type of treatment: occlusion must go on for periods of up to 2-3 weeks before lesions are cleared; and the recurrence rate is high, that is, the lesions return within a few weeks to a few months after withdrawal of therapy.

5-Fluorouracil has also been used in the topical treatment of psoriatic lesions under occlusion. However, when used alone erosions must be produced in order to have a lasting effect (Tsuji and Sugai, Arch. Derm., 105:208, 1973), and these erosions are painful to the patient. 5-Fluorouracil is a known inhibitor of thimydylate synthetase and through this inhibition also interferes with the nucleic acid metabolism.

SUMMARY OF THE INVENTION

It has now been discovered that corticosteroids and especially halogenated corticosteroids in combination with 5-fluorouracil and a suitable topical pharmaceutical carrier provide a synergistic formulation which is more effective than the compounds used alone and which provides a substantial improvement in recurrence. That is, the claimed formulation temporarily alleviates the symptoms of psoriasis, that is, improves the appearance of psoriatic skin by eliminating the psoriatic plaques with fewer side effects and a longer remission time than the compounds used alone.

DETAILED DESCRIPTION OF THE INVENTION

5-Fluorouracil is a known compound and is commercially available. The amount of 5-fluorouracil which may be used in the present invention varies from about 0.05 to about 10% and preferably about 1 to about 5% by weight of the composition.

Corticosteroids including halogenated corticosteroids are also known and are commercially available. Typical examples include cortisone, hydrocortisone and derivatives thereof including cortodoxone, flucetonide, fludrocortisone acetate, flurandrenolone acetonide, medrysone; prednisone, prednisolone and derivatives thereof including amcinafal, amcinafide, betamethasone benzoate, valerate and dipropionate, chloroprednisone acetate, descinalone acetonide, desonide, dexamethasone, dichlorisone acetate, difluprednate, flucloronide, flumethasone, flunisolide acetate, fluocinolone acetonide, fluocinonide, fluocortolone, fluorometholone, fluperoline acetate, fluprednisolone valerate, meprednisone, methyl prednisolone, paramethasone acetate, prednisolomate, prednisolone acetate, butylacetate and phosphate sodium, and triamcinolone acetonide, hexacetonide, diacetate, hydrocortisone butyrate, flumethasone pivalate, halcininide and clobetasol propionate.

The amount of corticosteroid which may be used in the present invention varies from about 0.01 to about 5% and preferably about 0.025 to about 0.1% by weight of the composition.

Conventional topical formulations may be used with the foregoing ingredients. For example, a typical formulation may contain non-ionic emulsifying waxes such as Polawax or fatty alcohols, glycol ethers or esters of fatty acids, other wax-like emulsifiers or self-emulsifying fatty alcohol blends; emollients, such as isopropyl myristate or other isopropyl esters of fatty acids, butyl esters of fatty acids, glycerin, propylene glycol, alcohols, dimethyl sulfoxide, dimethyl formamide, propylene glycol carbonate and other carboxylic acid esters; an oil phase such as mineral oil, petroleum oil, oil extracts from animal sources, e.g. shark oil, lanolin and oil extracts from vegetable sources, e.g. peanut oil. The formulation may also include stabilizers including, for example, EDTA, 8-OH quinoline and conventional antioxidants and preservatives.

A typical formulation for topical use contains the following ingredients per gram:

|  | Mg |
| --- | --- |
| halogenated corticosteroid | 1 |
| 5-fluorouracil | 10 |
| inert carrier | 989 |

In carrying out the novel method employing the topical route, the active ingredient formulated, for example, as an ointment or solution, as indicated above, is applied to a psoriatic lesion at a rate varying from 1 mg per square cm. of skin surface per day up to 10 mg per square cm. of skin surface per day until the appearance of the psoriatic skin has returned to normal. The ointment or solution is generally applied daily for one week, preferably using a continuous occlusive dressing. With the foregoing concentration, a dose of about 10–150 mg of the composition per square cm./per week of skin surface readily supplies the amount of active ingredient specified above.

To illustrate the manner in which the invention is made, the following examples are given. It is understood, however, that the examples are for purposes of illustration and the invention is not to be regarded as limited to any of the specific materials or conditions therein.

EXAMPLE

Method

Ninety subjects with nummular and extensive psoriasis were selected from a clinical pool. All were hospitalized for 7 to 9 days to control the treatment method and period. Psoriatic-involved portions of the body were divided into comparable separate areas and were treated with the following formulations, respectively, twice a day for 7 days. All treated areas were occluded 24 hours per day. Sixty of the ninety treated patients were able to be evaluated three months after the end of the treatment.

| Formulation | 5-Fluorouracil[1] | Corticosteroid[2] | Corticosteroid[3] |
|---|---|---|---|
| 1 | 1% | 0.025% | — |
| 2 | 1% | — | 0.1% |
| 3 | 1% | — | — |
| 4 | — | 0.025% | — |
| 5 | — | — | 0.1% |

[1] Fluoroplex, Allergan Pharmaceuticals.
[2] Commercially available hologenated corticosteroid formulation synalar (active steroid fluocinolone acetonide).
[3] Commercially available hologenated corticosteroid formulation valisone 0.1% (active steroid beta-methasone vaterale).

Results of the foregoing tests were as follows:
Formulations 1 and 2
 (a) Complete clearing of plaques in 7 days in 51 out of 60 patients (85%).
 (b) Recurrence within three months 22 out of 51 patients (43%).
Formulation 3
 (a) Complete clearing of plaques in 21 days in 31 out of 60 patients (52%).
 (b) Recurrence within three months 31 out of 31 patients (100%).
Formulations 4 and 5
 (a) Complete clearing of plaques in 21 days in 26 out of 60 patients (43%).
 (b) Recurrence within three months in 26 out of 26 patients (100%).

Comparing the foregoing formulations, it is apparent that formulations 1 and 2 are synergistic in that
 (1) they are far more effective than formulations 3, 4 and 5 (85% clearing of plaques in 7 days vs. 52% and 43% clearing of plaques in 21 days); and
 (2) they result in a far lower recurrence rate than formulations 3, 4 and 5 (43% recurrence vs. 100% recurrence).

I claim:

1. A method for treating psoriasis in humans comprising the topical administration to a human suffering from psoriasis of an effective dose for treating psoriasis of a composition comprising as active ingredients, from about 0.025 to about 0.1% by weight of β-methasone valerate and about 1 to about 5% of 5-fluorouracil.

2. A method for treating psoriasis in humans comprising the topical administration to a human suffering from psoriasis of an effective dose for treating psoriasis of a composition comprising as active ingredients, from about 0.025 to about 0.1% by weight of fluocinolone acetonide and about 1 to about 5% of 5-fluorouracil.

3. A composition for treating psoriasis in humans comprising as active ingredients, from about 0.025 to about 0.1% by weight of β-methasone valerate and about 1 to about 5% of 5-fluorouracil.

4. A composition for treating psoriasis in humans comprising as active ingredients, from about 0.025 to about 0.1% by weight of fluocinolone acetonide and about 1 to about 5% of 5-fluorouracil.

* * * * *